United States Patent [19]

Aaslid

[11] Patent Number: 4,817,621
[45] Date of Patent: Apr. 4, 1989

[54] APPARATUS INCLUDING DOPPLER SIGNAL TRANSDUCER FOR DETERMING THE POSITION OF AN OBJECT

[75] Inventor: Rune Aaslid, Seattle, Wash.

[73] Assignee: Eden Medizinische Elektronik GmbH, Überlingen, Fed. Rep. of Germany

[21] Appl. No.: 60,742

[22] Filed: Jun. 10, 1987

[30] Foreign Application Priority Data

Feb. 12, 1987 [DE] Fed. Rep. of Germany ....... 3704339

[51] Int. Cl.$^4$ .............................................. A61B 10/00
[52] U.S. Cl. ................................................. 128/662.03
[58] Field of Search ................. 33/441, 438; 128/380, 128/660, 97, 662.03; 73/861.25, 861.28, 861.26

[56] References Cited

U.S. PATENT DOCUMENTS

| | | | |
|---|---|---|---|
| 3,777,740 | 12/1973 | Hokanson | 128/663 |
| 4,381,787 | 5/1983 | Hottinger | 128/660 |
| 4,399,822 | 8/1983 | Theumer | 128/660 |
| 4,401,123 | 8/1983 | Baba | 128/660 |
| 4,421,118 | 12/1983 | Dow et al. | 128/660 |
| 4,431,007 | 2/1984 | Amazeen et al. | 128/660 |
| 4,495,816 | 1/1985 | Schlumberger | 128/660 |
| 4,601,292 | 7/1986 | Fidel et al. | 128/863 |

Primary Examiner—Francis Jaworski
Assistant Examiner—George Manuel
Attorney, Agent, or Firm—Becker & Becker, Inc.

[57] ABSTRACT

An apparatus for determining the position of an object or measuring point via a measuring element that is embodied as a Doppler signal emitter and receiver. Two parallelogram-type linkage systems, each having two ends, are provided, with one end being pivotably connected to the measurng element, and the other end being pivotably connected to a respective reference element, with the reference elements being disposed at a given angle to one another. The measuring element is pivotably connected in such a way as to be movable in a random fashion about an adjustable point.

14 Claims, 4 Drawing Sheets

APPARATUS INCLUDING DOPPLER SIGNAL TRANSDUCER FOR DETERMING THE POSITION OF AN OBJECT

BACKGROUND OF THE INVENTION

1. Field of the Invention

The present invention relates to an apparatus for determining the position and condition of an object, for example the position of a blood vessel and direction in which the blood flows in this vessel, via a measuring element that is embodied as a Doppler signal emitter and receiver.

2. Description of the Prior Art

To determine the position of blood vessels or other objects, and the rate with which liquids flow therein, supersonic radiation emitters and receivers are known via which reflected Doppler frequencies can be measured. The values recorded can be evaluated without difficulty with the aid of a data-display unit.

The measuring element, which operates as an emitter and receiver, is initially manually aligned or oriented, and is then moved in a random fashion in order to locate or detect the object that is to be measured, and to receive different signals that permit appropriate conclusions to be made. Although the distance between the measuring element and a blood vessel, and hence the approximate position thereof, can be determined in this manner, it is not possible to obtain an exact measurement, since variations are essential where the random movement is carried out manually. It is also impossible to repeat the measurements with any accuracy, since the random-type movements can be reproduced only imprecisely.

It is therefore an object of the present invention to provide an apparatus of the aforementioned general type with which it is possible, with extremely straightforward means, to align or orient the measuring element and to carry out a random movement, about a predetermined point, to determine values along the x and y axes, so that it is readily possible to achieve a three-dimensional pictorial representation of the position, for example of a blood vessel, and also the direction of the blood flowing therein, since the distance is also to be determined, all this being done with the aid of the signals emitted by the measuring element. Thus a blood vessel of a patient can be measured precisely in a short period of time. The cost for such an apparatus should be kept low, and the apparatus should be easy to handle and, should be capable of being operated as easily as possible. Above all, however, it should be possible to very precisely repeat measurements and to fix the measuring element in certain positions in order to be able to repeat measurements without difficulty at a later point in time in order to determine whether any changes have occurred.

BRIEF DESCRIPTION OF THE DRAWINGS

These objects, and other objects and advantages of the present invention, will appear more clearly from the following specification in conjunction with the accompanying schematic drawings, in which.

SUMMARY OF THE INVENTION

Figure 1:
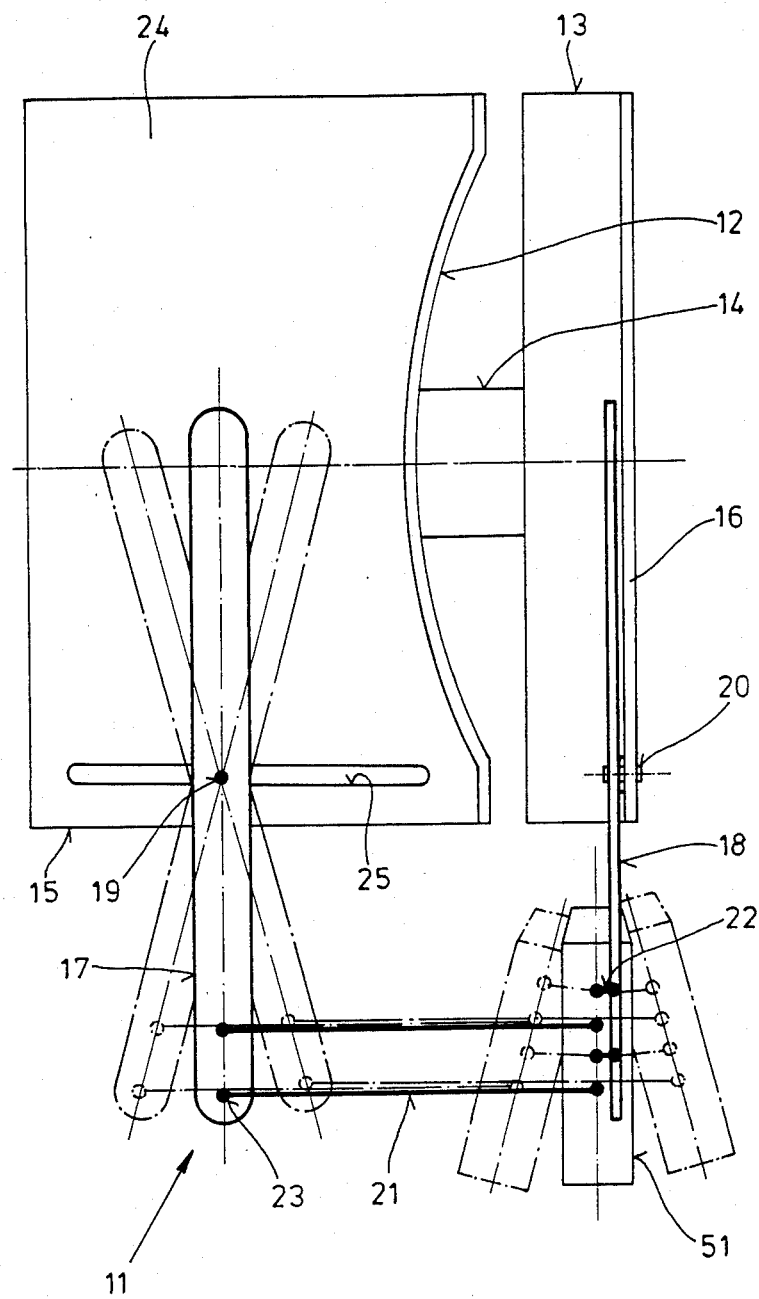
FIG. 1 is a plan view of one exemplary embodiment of the inventive apparatus.

The apparatus of the present invention is characterized primarily by two parallelogram-like linkage systems, each having two ends, one of which is pivotably connected to the measuring element, and the other of which is pivotably connected to a respective reference element, with the reference elements being disposed at a given angle to one another. The measuring element is preferably pivotably connected in such a way as to be pivotable about an adjustable point.

The reference elements are expediently rigidly interconnected by a bracket at an angle of 90° relative to one another. The reference elements are furthermore expediently held on the bracket in such a way as to be pivotable and/or adjustable in height about an axis determined by the respectively associated coordinates.

Those ends of the parallelogram-like linkage systems remote from the measuring element are advantageously supported on respective connecting lever arms that are pivotably held in an intermediate member that is mounted on the associated reference element.

Each of these intermediate members, which carry the connecting lever arms, can be embodied as a support plate for a recording assembly or the like, with this support plate being disposed perpendicular to the reference elements. In this connection, it is advisable to have the pivot points between the connecting lever arms and the intermediate elements be adjustable, for example via elongated slots formed in the intermediate members. However pursuant to a modified inventive it is also possible to provide, as intermediate members, adjusting levers that are pivotably mounted on the reference elements, preferably perpendicular thereto.

In a straightforward manner, the adjustment movements of the connecting lever arms and/or of the adjusting levers can be evaluated via potentiometers. To avoid strain, it is also suitable to hinge the linkage systems to the measuring element and the connecting lever arms via ball-type joints.

With the apparatus of the present invention, it is possible with extremely straightforward means to orient or align the measuring element relative to an object and to move the measuring element in a random fashion, so that measured values can be obtained in three planes, and hence a three-dimensional illustration of an object can be obtained, for example by scanning the object with supersonic radiation. If the measuring element is attached to two reference elements via two parallelogram-like linkage systems in such a way that it can move in a random fashion, such a random movement of the measuring element, which operates pursuant to the pulsed supersonic Doppler principle, can be produced manually about a selectable point. However, the movements along the x and y axes are easy to determine and plot, so that the position of a scanned object can be determined precisely with no difficulty in a short period of time, especially since the distance between the object and the measuring element can also be easily measured This makes it possible, without great effort, to repeat the measuring procedures as desired, since the measured values, once determined, can be recorded and are available for repeating the measurements. Accordingly, via a simple operation, with the aid of the inventive apparatus, which can also be adjusted in a planar manner along two coordinates, and hence can be aligned or oriented with no difficulty relative to the object that is to be measured, this object can be "pictured" three-dimensionally and the direction of the liquid flowing in this object can be easily determined.

Further specific features of the present invention will be described in detail subsequently.

DESCRIPTION OF PREFERRED EMBODIMENTS

Figure 2:
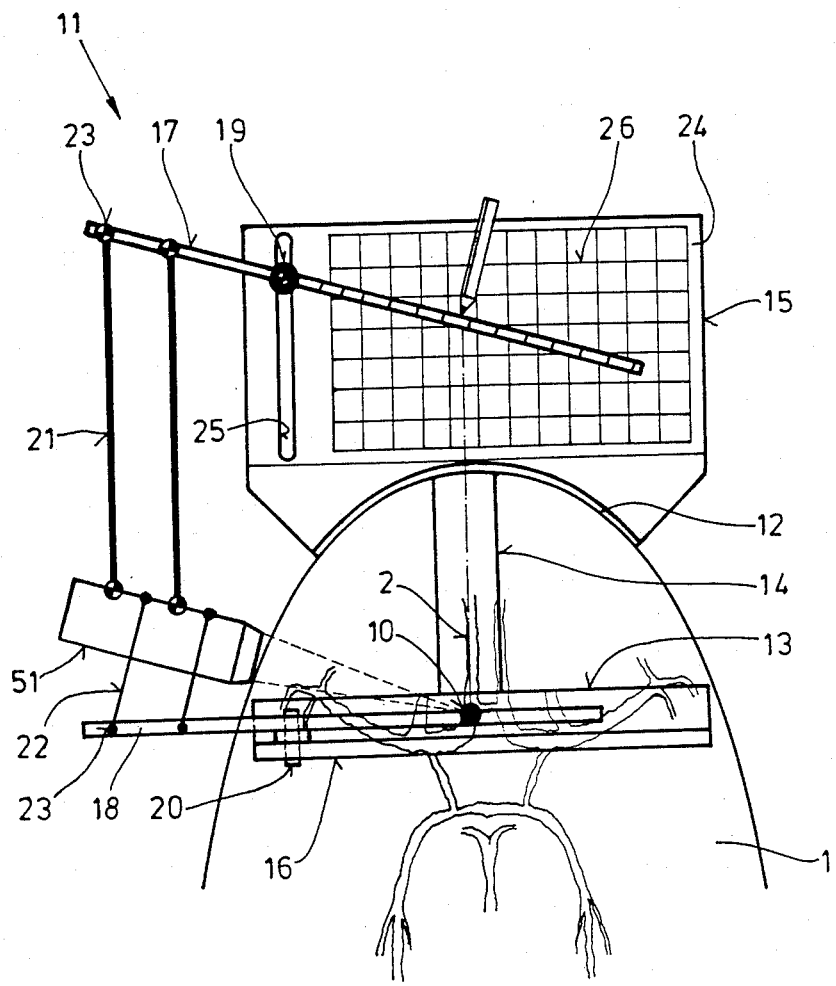
FIG. 2 is a view that shows the apparatus of FIG. 1 in an operative position.

Referring now to the drawings in detail, the apparatus illustrated in FIGS. 1 and 2 is designated by the reference numeral 11 and serves for determining the position of an object, for example a blood vessel 2 in a skull 1. The apparatus 11 essentially comprises a measuring element 51 that can be manually moved about a measuring point 10 in a random fashion. For this purpose, by means of two parallelogram-like linkage systems 21 and 22, the measuring element 51 is pivotably attached to reference elements 12 and 13 that are to be placed against the skull 1. By means of a bracket 14, the reference elements 12 and 13 are interconnected at a prescribed angle, and expediently extend at right angles to one another. At their free ends, each linkage system 21, 22 respectively is hinged to a connecting lever arm 17 or 18 and, via pivot pins 19 and 20, these are pivotably held on intermediate members 15 and 16 that are connected to the reference elements 12 and 13. By means of ball-type joints 23, the parallelogram-like linkage systems 21 and 22 are secured not only to the measuring element 51 but also to the connecting lever arms 17 and 18.

In the embodiment illustrated in FIGS. 1 and 2, each of the intermediate members 15 and 16 is embodied as a support 24 for a recording assembly 26, so that the movements of the adjusting or connecting lever arms 17 and 18 can be easily recorded, and/or the position of the measuring element 51 can be fixed. Furthermore, the pivot pins 19 and 20 can be shifted in elongated slots 25 of the supports 24: tthus, the measuring element 51 can also be easily moved in a planar fashion in order to initially align or orient the measuring element 51 relative to the object that is to be measured.

Consequently, with the aid of the measuring element 51, which can be moved in a planar and random fashion, the measuring point 10 can not only be plotted and evaluated without difficulty, but the position thereof can also be determined as a function of the measuring element. Thus, without requiring a lot of time and effort, repeated measurements of a blood vessel can be carried out in a short period of time since the measuring element 51 is easy to position due to the recorded values.

Figure 3:
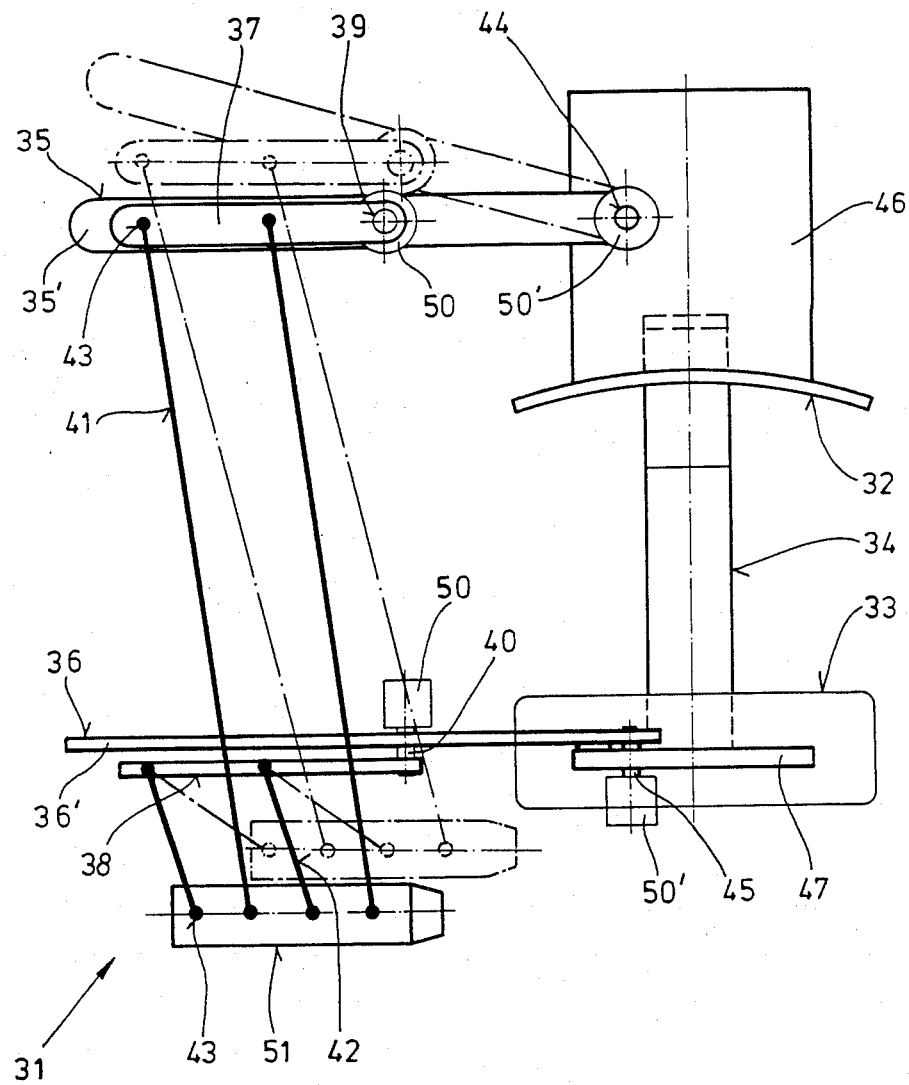
FIG. 3 is a plan view of another exemplary embodiment of the inventive apparatus.
Figure 4:
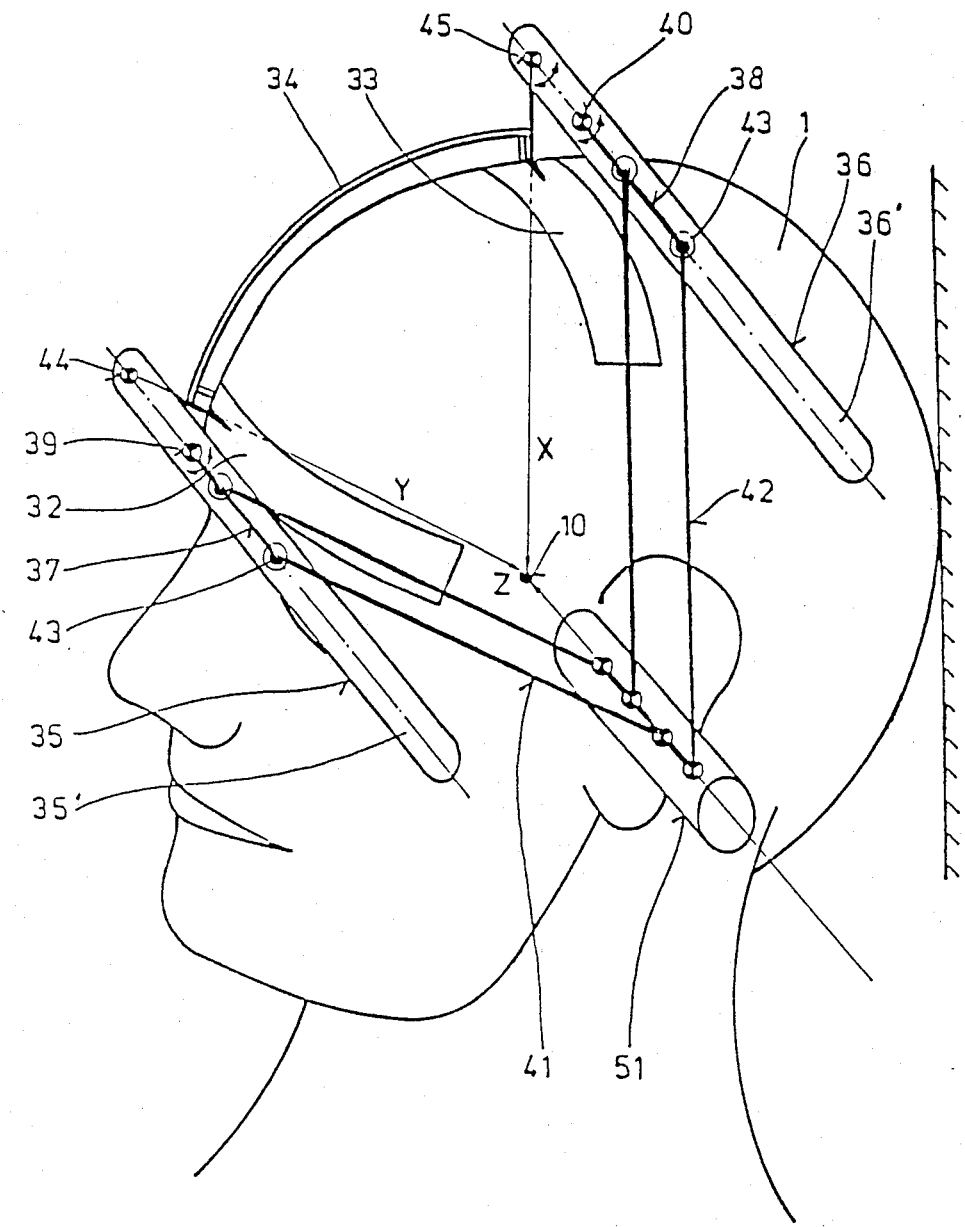
FIG. 4 is a view that shows the apparatus of FIG. 3 in an operative position.

In the embodiment of the apparatus 31 illustrated in FIGS. 3 and 4, the measuring element 51 is similarly attached by means of two parallelogram-like linkage systems 41 and 42 in such a way that it can move in a random fashion. Via intermediate members 35 and 36 that are embodied as adjusting levers 35' and 36', the linkage systems 41 and 42 are mounted to the reference elements 32 and 33. For this purpose, plates 46 and 47 are mounted on the reference elements 32 and 33, which are disposed at right angles to one another via a bracket 34. With the aid of pivot pins 44 and 45, the adjusting levers 35' and 36' are pivotably held in the plates 46 and 47. Via connecting lever arms 37 and 38, as well as pivot pins 39 and 40, the free ends of the parallelogram-like linkage systems 41 and 42 are hinged to the adjusting levers 35' and 36'.

With the aid of the adjusting levers 35' and 36', the measuring element 51 can be aligned in a planar fashion relative to a sound-permeable spot, as indicated in FIG. 3 by a dot-dash line. The random movement that is subsequently to be undertaken makes it possible to move the sound wave or ray over a large area, so that the object that is to be measured can be located rapidly. And since with the aid of potentiometers 50 and 50', not only the adjustment movements of the connecting lever arms 37 and 38, but also of the intermediate members 35 and 36, and hence of the measuring element 51, can be determined, an exact determination of the position of the blood vessel 2 can be undertaken via the coordinates x and y, as well as via the distance z of the measuring point 10 that is irradiated by the measuring element 51. Furthermore, the rate with which the blood flows in the vessel 2, and the direction in which it flows, can be determined with the aid of the supersonic radiation. Since the parallelogram-like linkage systems 41 and 42 are hinged via ball-type joints 43 to the measuring element 51 and the connecting lever arms 37 and 38, a random-type movement can easily be carried out manually.

The present invention is, of course, in no way restricted to the specific disclosure of the specification and drawings, but also encompasses any modifications within the scope of the appended claims.

I claim:

1. An apparatus for determining the position and other characteristics of an object, including for example the position of a blood vessel and rate as well as the direction in which the blood flows in this vessel, via a measuring element that is embodied as a Doppler signal emitter and receiver aligned as well as oriented to locate, to detect and to receive different signals that permit appropriate conclusions to be made, said apparatus further comprising:

two parallelogram-type linkage systems, each having two ends, one end of each system being pivotably connected via pivot means to said measuring element, and the other end of each system being pivotably connected via further pivot means to a respective reference element, said respective reference elements as well as said measuring element in structural relationship to very precisely repeat measurements and to fix the measuring element in certain positions in order to repeat measurements without difficulty at a later point in time to determine whether any changes have occurred.

2. An apparatus according to claim 1, in which said pivot means are ball-type joints that hinge the linkage systems to said measuring element and connecting lever arms that to avoid strain are pivotably connected collectively in such a way so as to be movable in a random fashion about an adjustable point.

3. An apparatus according to claim 2, which includes a bracket that rigidly interconnects said reference elements in such a way that the latter are disposed at an angle of 90° to one another.

4. An apparatus for determining the position and other characteristics of an object via a measuring element that is embodied as a Doppler signal emitter and receiver, said apparatus further comprising:

two parallelogram-type linkage systems, each having two ends, one end of each system being pivotably connected via pivot means to said measuring element, and the other end of each system being pivotably connected via pivot means to one of two reference elements, with said reference elements being disposed at a given angle to one another;

said measuring element being pivotably connected in such a way as to be movable in a random fashion about an adjustable point;

a bracket that rigidly interconnects said reference elements in such a way that the latter are disposed at an angle of 90° to one another; and a respective intermediate member mounted on each of said reference elements; and each of said other ends of said parallelogram-type linkage systems, which other ends are remote from said measuring element, being pivotably connected to a respective connecting lever arm, each of which is pivotably connected to a respective one of said intermediate members.

5. An apparatus according to claim 4, in which said reference elements are mounted on said bracket in such a way that they are pivotable.

6. An apparatus according to claim 4, in which said reference elements are mounted on said bracket in such a way that they are adjustable in position.

7. An apparatus according to claim 4, in which said reference elements are mounted on said bracket in such a way that they are pivotable and adjustable in position.

8. An apparatus according to claim 4, in which at least one of said intermediate members is in the form of a support plate for a recording unit, with said at least one intermediate member being disposed perpendicular to its associated reference element.

9. An apparatus according to claim 4, in which said connecting lever arms are adjustably pivotably connected via pivot means to said intermediate members.

10. An apparatus according to claim 9, in which said connecting lever arms are pivotably connected to said intermediate members via pivot pins; and in which said intermediate members are provided with elongated slots for said pivot pins to effect said adjustability of said pivotable connected between said connecting lever arms and said intermediate members.

11. An apparatus according to claim 4, in which said intermediate members are each in the form of a lever that is pivotably mounted on one of said reference elements via pivot means.

12. An apparatus according to claim 11, in which each of said adjusting levers is pivotable in a plane disposed perpendicular to the associated reference elements.

13. An apparatus according to claim 4, which includes potentiometers connected to, and serving to evaluate the movements of, at least one of the group consisting of said connecting lever arms and said intermediate members.

14. An apparatus according to claim 4, in which said pivot means that provide said pivotable connections between said parallelogram-type linkage systems and said measuring element on the one hand, and said linkage systems and said connecting lever arms on the other hand, are in the form of respective ball-type joints.

* * * * *